(12) United States Patent
Vardi et al.

(10) Patent No.: US 7,892,222 B2
(45) Date of Patent: *Feb. 22, 2011

(54) IMPLANTABLE DEVICE

(75) Inventors: Pnina Vardi, Haifa (IL); Yosef Gross, Moshav Mazor (IL); Konstantin Bloch, Petach-Tikya (IL); Daria Bloch, Petach-Tikva (IL); Nizza Boukobza, Harei Jehudah (IL)

(73) Assignee: Beta O 2 Technologies Ltd., Haifa (IL)

( * ) Notice: Subject to any disclaimer, the term of this patent is extended or adjusted under 35 U.S.C. 154(b) by 1824 days.

This patent is subject to a terminal disclaimer.

(21) Appl. No.: 10/466,069

(22) PCT Filed: Jan. 12, 2001

(86) PCT No.: PCT/IL01/00031

§ 371 (c)(1),
(2), (4) Date: Mar. 12, 2004

(87) PCT Pub. No.: WO01/50983

PCT Pub. Date: Jul. 19, 2001

(65) Prior Publication Data

US 2004/0133188 A1    Jul. 8, 2004

(51) Int. Cl.
*A61K 9/22* (2006.01)

(52) U.S. Cl. .................. 604/891.1; 604/93.01; 604/500; 604/502

(58) Field of Classification Search ............. 604/891.1, 604/890.1, 6.14, 6.16, 288.01–288.04, 93.01, 604/500, 502; 435/41, 69.4, 289.1, 292.1, 435/293.1, 293.2; 424/93.1, 93.2, 93.7, 195.17
See application file for complete search history.

(56) References Cited

U.S. PATENT DOCUMENTS

| | | | |
|---|---|---|---|
| 4,352,883 A | 10/1982 | Lim | |
| 4,402,694 A | 9/1983 | Ash et al. | |
| 4,631,053 A | 12/1986 | Taheri et al. | |
| 4,721,677 A | 1/1988 | Clark, Jr. | |
| 5,011,472 A | 4/1991 | Aebischer et al. | |
| 5,101,814 A | 4/1992 | Palti | |
| 5,116,494 A | 5/1992 | Chick et al. | |
| 5,262,055 A | 11/1993 | Bae et al. | |

(Continued)

FOREIGN PATENT DOCUMENTS

WO    WO 00/78920    12/2000

(Continued)

OTHER PUBLICATIONS

Klueth, et al., "Enhancement of implantable glucose sensor function in vivo using gene transfer-induced neovascularization", Biomaterials, vol. 26, No. 10, Apr. 2005. (an abstract).

(Continued)

*Primary Examiner*—Theodore J Stigell
(74) *Attorney, Agent, or Firm*—The Nath Law Group; Jerald L. Meyer; Sungyeop Chung (57) ABSTRACT

A device for implanting in the body. The device comprises a chamber containing cells. The device also comprises an oxygen generator for providing oxygen to the cells.

33 Claims, 4 Drawing Sheets

U.S. PATENT DOCUMENTS

| | | |
|---|---|---|
| 5,427,935 A | 6/1995 | Wang et al. |
| 5,614,378 A * | 3/1997 | Yang et al. .................... 435/41 |
| 5,713,888 A * | 2/1998 | Neuenfeldt et al. ...... 604/891.1 |
| 5,741,334 A | 4/1998 | Mullon et al. |
| 5,834,005 A | 11/1998 | Usala |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 6,091,974 A | 7/2000 | Palti |
| 6,368,592 B1 * | 4/2002 | Colton et al. .............. 424/93.7 |
| 6,372,244 B1 | 4/2002 | Antanavich et al. |
| 2003/0050622 A1 | 3/2003 | Humes et al. |
| 2003/0087427 A1 | 5/2003 | Colton et al. |
| 2005/0136092 A1 | 6/2005 | Rotem et al. |
| 2007/0190038 A1 | 8/2007 | Suzuki |
| 2008/0086042 A1 | 4/2008 | Brister et al. |
| 2009/0012502 A1 | 1/2009 | Rotem et al. |

FOREIGN PATENT DOCUMENTS

| | | |
|---|---|---|
| WO | WO 2009/031154 | 3/2009 |

OTHER PUBLICATIONS

An office Action dated May 14, 2010, which issued during the prosecution of Applicant's U.S. Appl. No. 12/315,102.

An International Search Report and a Written opinion, both dated Jun. 9, 2010, which issued during the prosecution of Applicant's PCT/IL09/01114.

Stagner, et al., "The pancreas as an islet transplantation site", Sep. 1, 2007, Journal of the Pancreas, vol. 8, No. 5, pp. 628-636.

An International Search Report and a Written opinion, both dated Jan. 25, 2010, which issued during the prosecution of Applicant's PCT/IL09/00905.

* cited by examiner

IMPLANTABLE DEVICE

FIELD OF THE INVENTION

The present invention is in the field of devices implantable in a body, and more specifically to implanted devices containing living cells.

BACKGROUND OF THE INVENTION

Several disorders arising from hyposecretion of one or more substances such as hormones are known. Among these are diabetes, Parkinson's disease, Alzheimer's disease, hypo- and hyper-tension, hypothyroidism, and various liver disorders. The hormone insulin, for example, is produced by $\beta$-cells in the islets of Langerhans of the pancreas. In normal individuals, insulin release is regulated so as to maintain blood glucose levels in the range of about 70 to 110 milligrams per deciliter. In diabetics, insulin is either not produced at all (Type 1 diabetes), or the body cells do not properly respond to the insulin that is produced (Type 2 diabetes). The result is elevated glucose levels in the blood.

Disorders arising from hyposecretion of a hormone are usually treated by administration of the missing hormone. However, despite advances in understanding and treating many of these diseases, it is often not possible to precisely regulate metabolism with exogenous hormones. A diabetic, for example, is required to make several daily measurements of blood insulin and glucose levels and then inject an appropriate amount of insulin to bring the insulin and glucose levels to within the acceptable range.

Organ transplantation is not a viable treatment today for most of these disorders for several reasons including rejection of a transplanted organ by the immune system. Isolated cells may be implanted in the body after being treated to prevent rejection, e.g. by immunosuppression, radiation or encapsulation. Methods of immunoprotection of biological materials by encapsulation are disclosed in U.S. Pat. Nos. 4,352,883, 5,427,935, 5,879,709, 5,902,745, and 5,912,005. The encapsulating material is selected so as to be biocompatible and to allow diffusion of small molecules between the cells of the environment while shielding the cells from immunoglobulins and cells of the immune system. Encapsulated $\beta$-cells, for example, can be injected into a vein (in which case they will eventually become lodged in the liver) or embedded under the skin, in the abdominal cavity, or in other locations. Fibrotic overgrowth around the implanted cells, however, gradually impairs substance exchange between the cells and their environment. Hypoxygenation of the cells ultimately leads to cell death.

U.S. Pat. No. 5,855,613 discloses embedding cells in a thin sheet of alginate gel that is then implanted in a body.

U.S. Pat. No. 5,834,005 discloses immunoisolating cells by placing them in a chamber that is implanted inside the body. In the chamber, the cells are shielded from the immune system by means of a membrane permeable to small molecules such as glucose, oxygen, and the hormone secreted by the cells, but impermeable to cells and antibodies. These implanted chambers, however, do not have a sufficiently high surface area to volume ratio for adequate exchange between the cells and the blood. Thus, also in this case, hypoxygenation ultimately leads to cell death.

SUMMARY OF THE INVENTION

The present invention provides an implantable device comprising a chamber for holding functional cells and an oxygen generator for providing oxygen to the cells within the chamber. The cells, referred to herein as "functional cells", are loaded into the chamber of the device that is then implanted in the body. The device comprises an oxygen generator, i.e. an element that can produce oxygen and make it available to the cells, so that the functional cells do not suffer from hypoxygenation. The oxygen generator thus produces oxygen and typically releases the oxygen in the cell's vicinity.

The chamber has walls, which are permeable to nutrients needed by the cells as well as substances produced or secreted by the cells, such substances including, for example, metabolites, waste products produced by the cells and substances needed by the individual produced by the functional cells. In the body, the functional cells are immunoisolated from body constituents by the chamber's walls while being continuously exposed to adequate concentrations of oxygen, nutrients and hormones which penetrate the chamber's walls. The fact that oxygen is supplied to the cells by the oxygen generator allows the functional cells to maintain a high metabolic rate, so that a smaller number of functional cells are required for a given effect, as compared to prior art devices. The device containing the functional cells may be implanted in various parts of the body such as under the skin or in the peritoneum. The device may have any shape as required by a particular application. In accordance with one embodiment of the invention, the device is configured as a thin tubular element containing the functional cell within the tube's lumen. The device is typically of a size such that it may be implanted by injection through an introducer such as a syringe. Such an implantation procedure may be short and last only about 10 minutes. Other shapes of the device, e.g. a wafer shape, are also contemplated within the scope of the invention.

In one embodiment, the oxygen generator comprises photosynthetic cells that convert carbon dioxide to oxygen when illuminated. The photosynthetic cells are preferably unicellular algae, for example, a high temperature strain of *Chlorella pyrenoidosa* (cat. No. 1230. UTEX) having an optimal temperature about equal to body temperature. Other photosynthetic cells that may be used with the invention include *Chlorella vulgaris, Scenedesmus obligus*, Euglena, Volvox, and Spirolina. The photosynthetic cells may be autotrophic or mixotrophic. Isolated chloroplasts may be used instead of, or in addition to, intact cells. In the case where the oxygen generator are photosynthetic cells the chamber comprises a light source, with an associated power source, such as a battery. The photosynthetic cells or chloroplasts may be contained within a separate compartment within the device, e.g. in the case of a device in the form of a tube, they may be contained within a thin elongated chamber contained within the tube (in essence a smaller diameter tube); or may be dispersed.

In another embodiment, the oxygen generator comprises a pair of electrodes. When an electric potential is applied across the electrodes, oxygen is released by electrolysis of ambient water molecules present within the chamber. The electrodes are connected to a power source, typically a rechargeable battery.

The chamber may further comprise an oxygen sensor that determines the oxygen concentration in the vicinity of the functional cells. A microprocessor may be provided to turn the oxygen generator when the sensor detects that the oxygen concentration is below a predetermined minimum and turns it off when the oxygen concentration is above a predetermined maximum.

The functional cells pancreatic islet cells ($\alpha$-cells, $\beta$-cells, etc.), hepatic cells, neural cells, renal cortex cells, vascular endothelial cells, thyroid cells, parathyroid cells, adrenal cells, adrenal cells, thymic cells ovarian cells, and testicular cells. In accordance with one currently preferred embodiment the functional cells are pancreatic β-cells, which are insulin-releasing cells. Such a device may be configured for use in the treatment of insulin-dependent diabetes or for monitoring glucose levels in the body. As another example, the functional cells may be hepatic cells, whereby the device can serve as an "artificial liver".

The functional cell population in the device may be in the form of individual, may be in the form of cell clusters, or as pieces of excised tissue. These tissues or cells include, without limitation, tissue or cells removed from a donor animal, tissue or cells obtained by incubation or cultivation of donor tissues and cells, cells obtained from viable cell lines, cells obtained by genetic engineering. The cells may be of human or animal origin as well as genetically engineered or cloned cells or stem cells. The cells may be autologous or heterologous with the recipient's cells. The tissues or cells may perform a useful function by secreting a beneficial substance into the body, such as hormones or neurotransmitters, or removing a harmful substance from the body by taking them up, such as in the case of hepatic cells which may take up various toxic substances. The cells, cell clusters or tissue pieces may be dispersed in a liquid medium or matrix within the chamber or may be attached to a substrate, e.g. the walls of the chamber.

In another application, the chamber of the present invention is used to implant cells in the body as part of a system for detecting or monitoring the level of a substance in body fluids. Such a system comprises an implantable device of the invention having a detector adapted to monitor a property of the functional cells that is correlated with the level of the substance in the medium surrounding the functional cells. For example, U.S. Pat. No. 5,101,814, discloses use of a chamber for implanting glucose sensitive cells into the body and monitoring an optical or electrical property of the cells that is correlated with glucose levels. The present invention may incorporate a detector arrangement of the kind disclosed in U.S. Pat. No. 5,101,814.

The present invention further concerns a method for treating an individual suffering from a substance-deficiency by implanting in the individual a device of the invention containing functional cells, which can secrete said substance. For example, if the individual suffers from insulin-dependent (type I) the functional cells may be pancreatic β-cells.

By another embodiment the method may employed for treating an individual suffering from a condition where a beneficial effect may be achieved by removal of a substance from the body, such as in cases of a liver mal-function. The functional cells, in accordance with this embodiment are capable of removal of such substance.

The present invention further concerns a method of monitoring level of a substance in an individual's body, comprising implanting the above system in the individual's body and monitoring the reading of said detector.

The power source in the device of the invention is typically a rechargeable battery. The device preferably comprises a recharging circuitry linked to said batter. For remote induction recharging of the battery as known per se. The device preferably comprises also an electronic circuitry for monitoring parameters of the device or its surrounding or for controlling operational parameters of the device. Such monitored parameters may be parameters influencing the functional cells' viability or the level of production of a needed substance e.g. the oxygen level; the level of a produced needed substance; the level in body fluids of a substance which is to be produced or removed by the device; etc. The monitored parameters may, for example, be used in order to control the level of oxygen production (by controlling the current to the electrodes or the light generated by the light source, as the case may be). The control circuitry may comprises means for wireless communication with an external device, as known per se.

BRIEF DESCRIPTION OF THE DRAWINGS

In order to understand the invention and to see how it may be carried out in practice, preferred embodiments will now be described, by way of non-limiting examples only, with reference to the accompanying drawings, in which:

FIG. 1 is a device according to a first embodiment of the invention;

FIG. 2 is a device according to a second embodiment of the invention;

FIG. 3 is a device according to a third embodiment of the invention: and

FIG. 4 is a device according to a fourth embodiment of the invention.

DETAILED DESCRIPTION OF PREFERRED EMBODIMENTS

First Embodiment

Figure 1A:
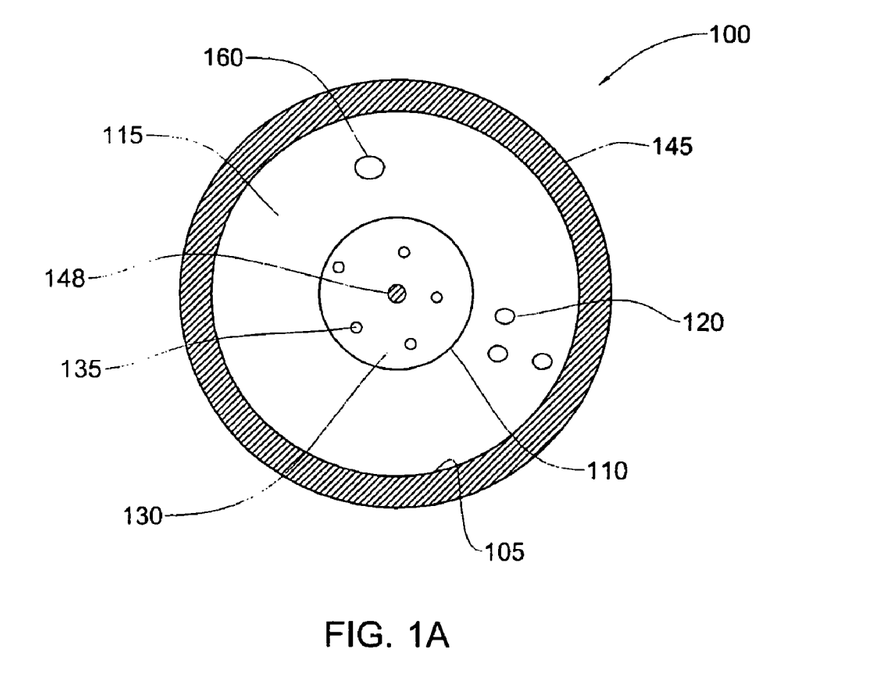
Figure 1B:
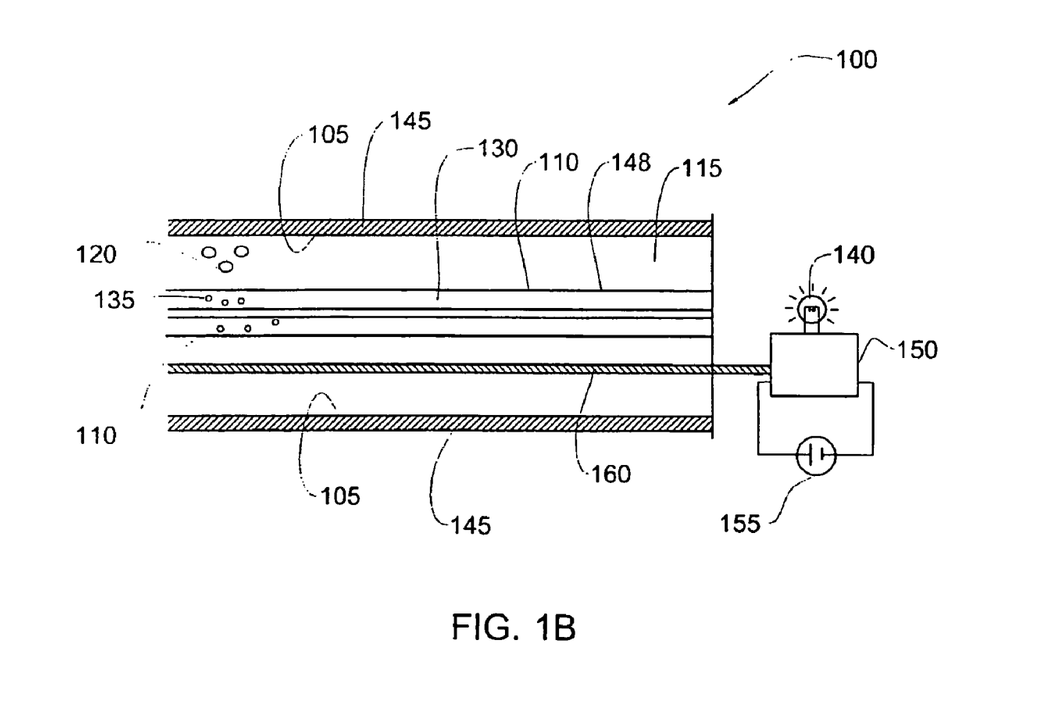

Referring first to FIG. 1, an embodiment of the device of the invention, is shown in cross-sectional (FIG. 1a) and longitudinal (FIG. 1b) view. The device has a chamber 100 having the overall shape of a thin cylinder. The chamber thus has an extremely large surface area to volume ratio allowing both efficient exchange of nutrients and waste and simple insertion and retrieval into and out of the peritoneum, or any other body area. The chamber 100 is flexible and may be made to assume any desired configuration in the body.

Outer membrane 105 is formed from a semipermeable material, for example, a polyvinyl chloride acrylic copolymer. The molecular weight cut-off of the outer membrane 105 is selected so that the outer membrane 105 is permeable to nutrients and active substances, such as hormones secreted by the cells but is impermeable to immunoglobulins and cells. The molecular weight cutoff of the outer membrane 105 is preferably between 10,000 and 70,000 Dalton. The outer membrane 105 has an anti-fibrin coating 145 that inhibits fibrotic overgrowth.

Inner membrane 110 is permeable to small inorganic molecules such as gases water and salts. The molecular weight cutoff of the inner membrane 110 is preferably between 100 and 200 Dalton. The inner membrane 110 may be made from materials commonly used for artificial lung membranes for example, such materials as are disclosed in U.S. Pat. No. 5,614,378. The interior 130 of inner membrane 110 contains photosynthetic cells 135. The photosynthetic organisms may be, for example, unicellular algae such as *Chlorella*. A light source 140 produces light preferably having a wavelength in the range of 400 to 700 nm. Light is guided from the light source 140 along the length of the chamber 100 by an optic fiber 148. The chamber 100 contains a microprocessor 150, a power source 155 that may be for example, a rechargeable battery or any other kind of power source, and an oxygen sensor 160. The photosynthetic cells 135 constitute an oxygen generator.

Prior to implantation of the chamber 100 into the recipient's body, functional cells 120 are loaded into the annular space 115 between outer membrane 105 and inner membrane 110. The functional cells 120 may be, for example, pancreatic islets, in which case about $10^6$ islets are sufficient to produce adequate amounts of insulin to regulate glucose levels in the recipient's body. The functional cells 120 may be suspended in a liquid medium in the annular space 115 or immobilized in the annular space 115 by embedding in a gel matrix formed, for example, from alginate, polylysine, chitosan, polyvinyl alcohol, polyethylene glycol, agarose, gelatin, or k-carrageenan.

After being loaded with the functional cells 120, the chamber 100 is implanted into the body by means of an applicator that may be, for example, a syringe. The processor 150, the light source 140 and the power source 155 may also be implanted in the body, or may in use be external to the body. If the light source 140 in use is external to the body, the optic fiber 148 is configured to pass through the skin. If the processor 150 in use is external to the body, the oxygen sensor 160 is configured to pass through the skin.

When oxygen sensor 160 detects that the oxygen level in the annular space 115 is below a predetermined minimum, the light source 140 is turned oil by the microprocessor 150 in order to induce photosynthesis by the photosynthetic cells 135. The oxygen produced by photosynthesis in photosynthetic cells 135 is released from the photosynthetic cells 135 and diffuses through the inner membrane 110 into the annular space 115 and is thus made available to the functional cells 120. When oxygen sensor 160 detects that the oxygen level in the annular space 115 is above a predetermined maximum, the light source 140 is turned off by the microprocessor 150 in order to stop photosynthesis by photosynthetic cells 135, so as to conserve the power source 155. About $10^9$-$10^{10}$ *Chlorella* cells are sufficient to produce an adequate supply of oxygen for $10^6$ functional islets.

The power source 155 may periodically be recharged when the chamber 100 is inside the body. For example, electrical contacts (not shown) normally located outside the body may be connected via a percutaneous cable to the terminals of the power source 155. An external voltage is then applied across the contacts so as to recharge the power source 155. Alternatively, the power source 155 may be recharged inductively by applying an electric field externally on the skin in the vicinity of the chamber 100.

Second Embodiment

Figure 2A:
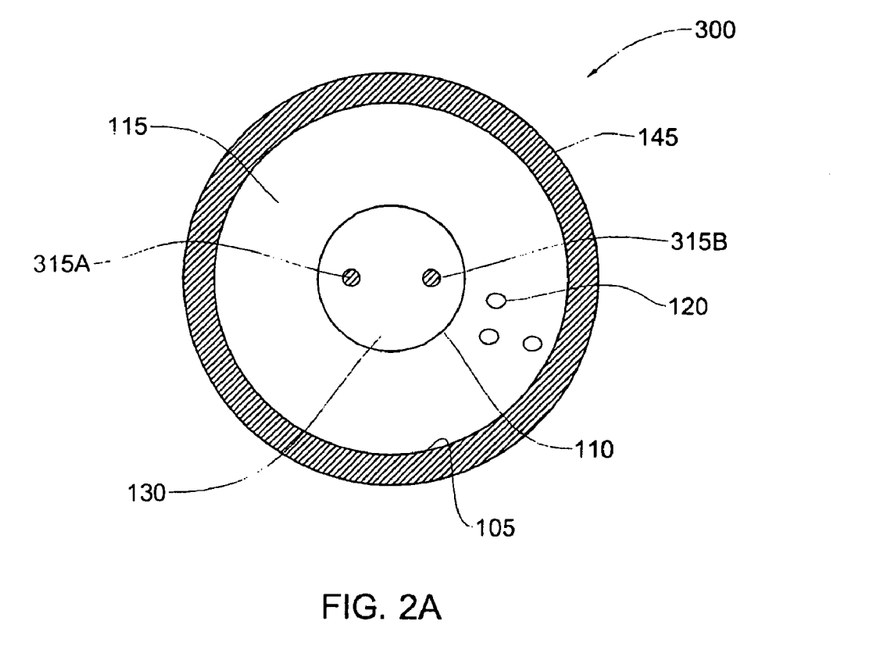
Figure 2B:
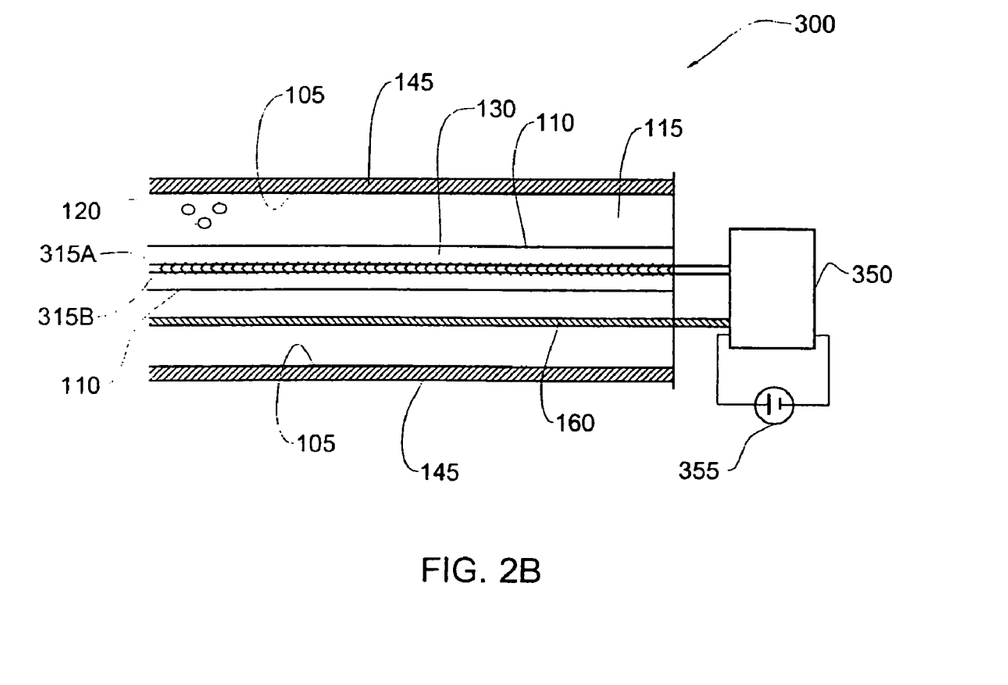

Referring now to FIG. 2, a second embodiment of the invention, is shown in cross-sectional (FIG. 2a) and longitudinal (FIG. 2b) view. This embodiment is similar to the first embodiment shown in FIG. 1, and identical components are identified by the same numeral. A pair of flexible electrodes 315a and 315b extends along the length of the chamber 300 in the interior 130 of the inner membrane 110. The electrodes are made of a biocompatible material such as carbon or platinum. The chamber 300 contains a power source 355, a microprocessor 350, and an oxygen sensor 160. The electrodes 315a and 315b constitute an oxygen generator.

Prior to insertion of the chamber 300 into the recipient's body, functional cells 120 are loaded into the annular space 115 between outer membrane 105 and inner membrane 110. The functional cells may be suspended in a liquid medium in the annular space 115 or immobilized by embedding the functional cells 120 in a gel matrix formed, for example, from alginate, polylysine, chitosan, polyvinyl alcohol, polyethylene glycol, agarose, gelatin, or k-carrageenan.

The chamber 300 is then implanted in the body using an applicator that may be, for example, a syringe. The processor 350 and the power source 355 may also be implanted in the body or may in use be external to the body. If the processor 350 in use is external to the body, the electrodes 315a and 315b and the oxygen sensor 160 are configured to pass through the skin.

In the body, when oxygen sensor 160 detects that the oxygen level in the annular space 115 is below a predetermined minimum, the microprocessor 350 causes an electric potential to be generated between the electrodes 315a and 315b by means of the power source 355. This causes hydrolysis of water molecules in the interior 130 of inner membrane 110, producing oxygen. The oxygen molecules diffuse through inner membrane 110 into the annular space 115 between inner membrane 110 and outer membrane 105, and is thus made available to the functional cells 120. When the oxygen sensor 160 detects that the oxygen level in the annular space 115 is above a predetermined maximum, the electrical potential across the electrodes 315a and 315b is turned off by microprocessor 350, so as to conserve the power source 155. The power source 155 may be recharged when the chamber 300 is inside the body as described in reference to the previous embodiment.

Third Embodiment

Figure 3A:
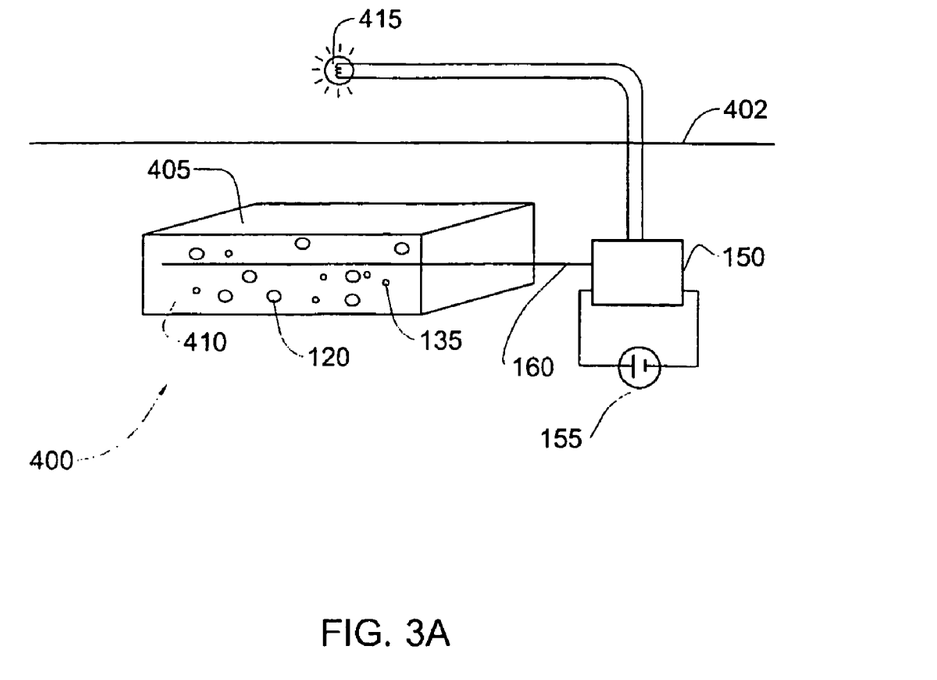

In FIG. 3, another embodiment of the invention is shown. This embodiment has components in common with the embodiment of FIG. 1 and similar components are identified with the same numeral. This embodiment has a chamber 400 that is formed as a thin planar or wafer-like shape that is implanted in the body close to the skin 402. The surface 405 of the chamber 400 closest to the skin 402 is transparent to light. The photosynthetic cells 135 and functional cells 120 are located in the interior 410 of the chamber 400. The photosynthetic cells 135 are irradiated with light from a light source 415 located outside the body. Light from the light source 415 penetrates through the skin 402 and the surface 405 to the interior 410 of the chamber 400. The processor 150 and the power source 155 may also be implanted in the body or may in use be located external to the body. The light source 415 may be integral with the device as shown in FIG. 3a. In this case when the oxygen sensor 160 detects that the oxygen level in the interior 410 of the device 400 is below a predetermined minimum, the light source 415 is turned on by the processor 150 in order to induce photosynthesis of the photosynthetic cells 135. When the oxygen sensor 160 detects that the oxygen level in the interior 410 is above a predetermined maximum, the light source 415 is turned off by the processor 150.

Figure 3B:
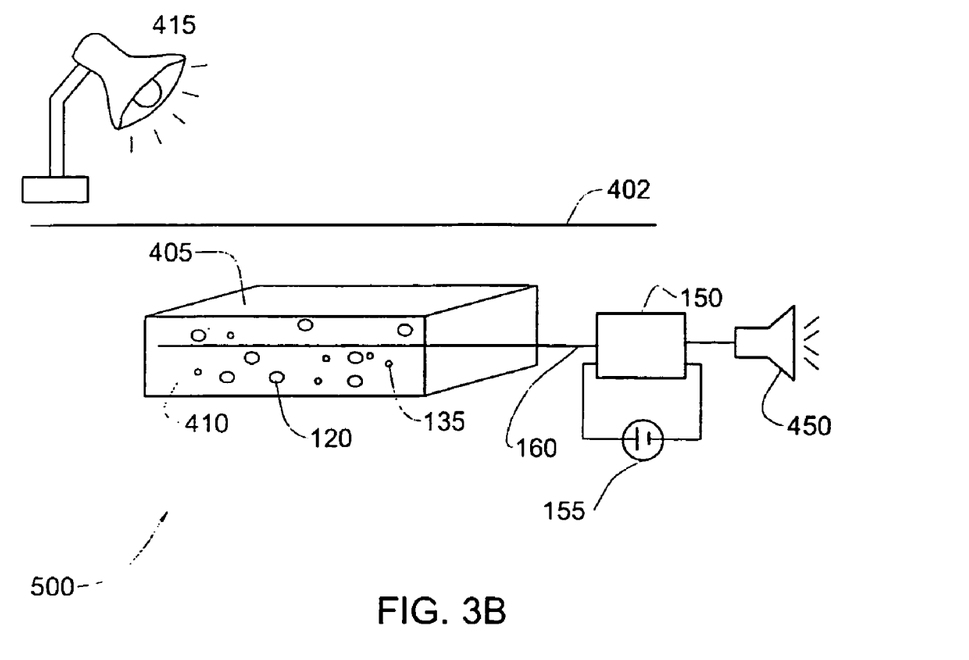

The photosynthetic cells may also be illuminated by a light source 415 that is independent of the processor 150 as shown in FIG. 3b. In this case when the oxygen sensor 160 detects that the oxygen level in the interior 410 of the device 400 is below a predetermined minimum, the processor 150 generates a sensible signal such as an audible signal produced by a loudspeaker 450. This indicates to the individual that he must irradiate the skin 402 overlying the chamber 400 in order to induce photosynthesis of the photosynthetic cells 135. When the oxygen sensor 160 detects that the oxygen level in the interior 410 is above a predetermined maximum, the processor 450 discontinues the sensible signal, thus informing the individual that the illumination should be stopped.

Fourth Embodiment

Figure 4A:
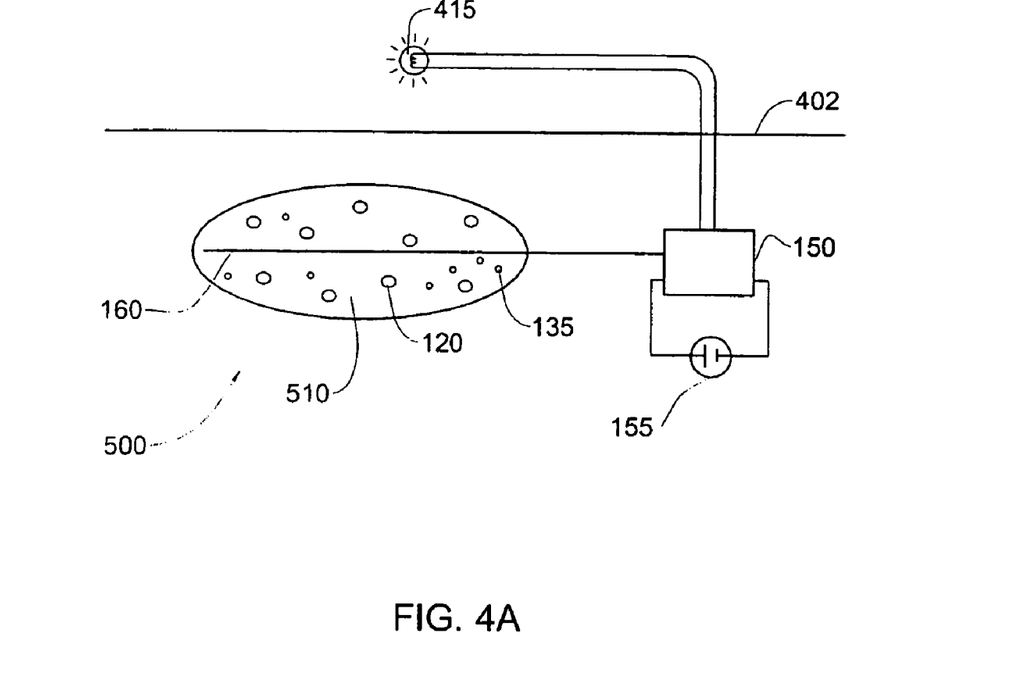

In FIG. 4, yet another embodiment of the invention is shown. This embodiment has components in common with the embodiment of FIG. 3 and similar components are identified with the same numeral. This embodiment has a chamber 500 that is formed from a solid gel such as alginate, polylysine, chitosan, polyvinyl alcohol, polyethylene glycol, agarose, gelatin, or k-carrageenan. The gel is preferably transparent to light. The photosynthetic cells 135 and functional cells 120 are embedded in the gel. The photosynthetic cells 135 are irradiated with light from a light source 415 located outside the body. Light from the light source 415 penetrates through the skin 402 and the gel to the photosynthetic cells. The processor 150 and the power source 155 may also be implanted in the body or may in use be located external to the body. The light source 415 may be integral with the device as shown in FIG. 4a. In this case when the oxygen sensor 160 detects that the oxygen level in the interior 510 of the device 400 is below a predetermined minimum, the light source 415 is turned on by the processor 150 in order to induce photosynthesis of the photosynthetic cells 135. When the oxygen sensor 160 detects that the oxygen level in the interior 510 is above a predetermined maximum, the light source 415 is turned off by the processor 150.

Figure 4B:
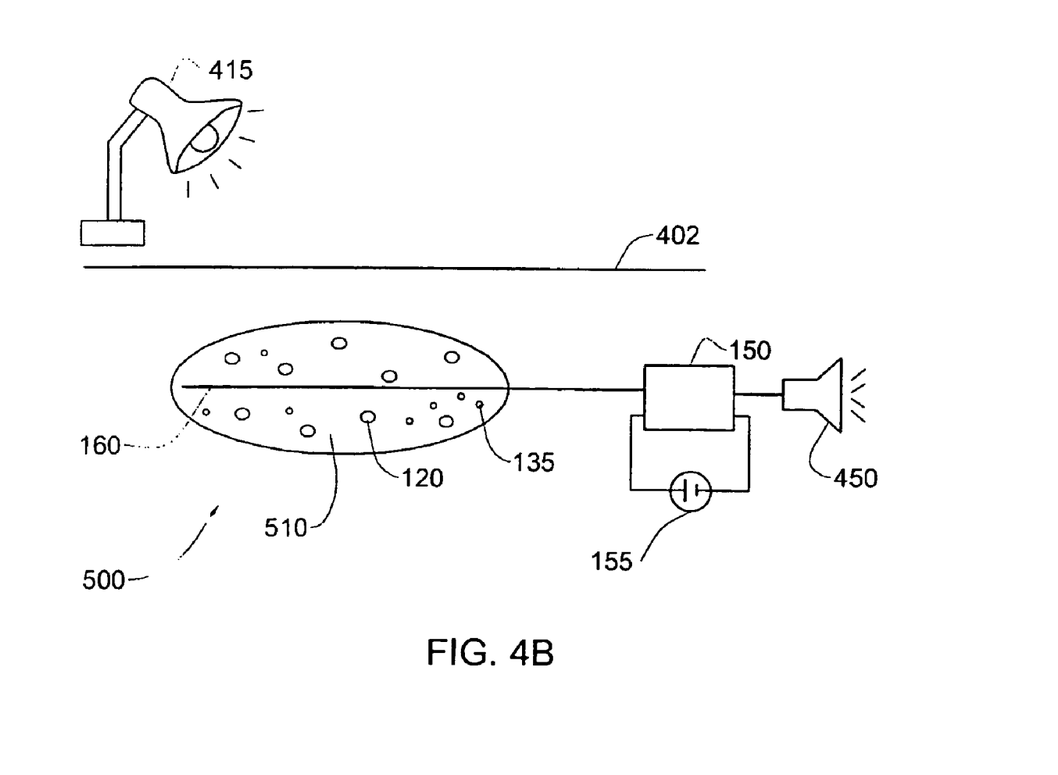

The photosynthetic cells may also be illuminated by a light source 415 that is independent of the processor 150 as shown in FIG. 4b. In this case when the oxygen sensor 160 detects that the oxygen level in the interior 510 of the chamber 500 is below a predetermined minimum, the processor 150 generates a sensible signal such as an audible signal produced by a loudspeaker 450. This indicates to the individual that he must irradiate the skin 402 overlying the chamber 500 in order to induce photosynthesis of the photosynthetic cells 135. When the oxygen sensor 160 detects that the oxygen level in the interior 410 is above a predetermined maximum, the processor 150 discontinues the sensible signal thus informing the individual that the illumination should be stopped.

The invention claimed is:

1. An implantable device comprising:
   a chamber holding isolated functional cells; and
   an oxygen generator for providing oxygen to the cells within the chamber, wherein the oxygen generator is disposed within the implantable device and comprises one or more photosynthetic units that produce oxygen when illuminated, the photosynthetic units positioned within the implantable device such that the oxygen produced is provided to the cells, and
   wherein the implantable device, as a whole, is implantable in the body of an individual.

2. A device according to claim 1, further comprising an oxygen sensor for determining oxygen concentration in a vicinity of the functional cells.

3. A device according to claim 2, further comprising a microprocessor configured to activate the oxygen generator when the oxygen concentration in the vicinity of the functional cells is below a first predetermined threshold, and to inactivate the oxygen generator when the oxygen concentration in the vicinity of the functional cells is above a second predetermined threshold.

4. The device according to claim 2, further configured to produce a sensible signal when the oxygen concentration is below a predetermined value.

5. A device according to claim 1, wherein the photosynthetic units comprise one or more photosynthetic cells.

6. A device according to claim 5, wherein the photosynthetic cells are algae.

7. A device according to claim 6, wherein the photosynthetic cells are unicellular algae.

8. A device according to claim 7, wherein the unicellular algae are of the species *Chlorella*.

9. A device according to claim 6, wherein the algae are genetically engineered algae.

10. The device according to claim 5, further comprising a light source.

11. The device according to claim 10, wherein the light source is configured to be implanted in the body.

12. The device according to claim 10, wherein the light source is configured to be placed external to the body.

13. The device according to claim 10, further comprising an optic fiber for conducting light from the light source to the photosynthetic cells.

14. A device according to claim 1, wherein the photosynthetic units comprise isolated chloroplasts.

15. The device according to claim 1, wherein the chamber has transparent walls.

16. A device according to claim 1, wherein the functional cells release a needed substance and the chamber has walls, which are permeable to said substance but not to said cells, whereby said substance is released to the body.

17. A device according to claim 16, wherein the functional cells are selected from the group consisting of: pancreatic islet cells, hepatocytes, thyroid cells, parathyroid cells, neural cells, ovarian cells, adrenal cells, renal cortex cells, vascular endothelial cells, thymic cells, ovarian cells, testicular cells, genetically engineered cells, cloned cells and stem cells.

18. A device according to claim 1, wherein the functional cells can absorb or degrade a substance from the body, and the chamber has walls, which are permeable to said substance but not to said cells, whereby said substance is drained from surroundings of the device into said chamber.

19. A device according to claim 1, comprising a rechargeable battery.

20. A device according to claim 19, comprising an electric circuit linked to said rechargeable battery for remote induction recharging of said battery.

21. A device according to claim 1, comprising an electronic circuitry for monitoring parameters of the device or its surrounding or controlling operational parameters of the device.

22. A device according to claim 21, wherein said circuitry comprises means for wireless communication with an external control or monitoring circuitry.

23. A device according to claim 1, wherein the functional cells comprise pancreatic β-cells.

24. An implantable device for treating a medical disorder comprising a chamber, which is configured to be implanted in a body of an individual, the chamber holding:
   isolated functional cells that produce a substance for treatment of the medical disorder, the chamber having a wall that is permeable to the produced substance; and
   photosynthetic cells that convert carbon dioxide to oxygen when illuminated,
   wherein the device, when entirely implanted within the body, is configured such that the photosynthetic cells can be illuminated.

25. The device according to claim 24, further comprising a light source.

26. The device according to claim 25, wherein the light source is configured to be implanted in the body.

27. A device according to claim 24, wherein the functional cells can release a needed substance, and the chamber has walls, which are permeable to said substance but not to said cells, whereby said substance is released to the body.

28. A device according to claim 27, wherein the functional cells comprise pancreatic β-cells.

29. A method of treating a medical disorder comprising:
   providing the device of claim 24;
   implanting the device in a body of an individual such that the photosynthetic cells can be illuminated; and when said device is implanted in the body, producing a treatment substance with said device and secreting said treatment substance to the body.

30. A method according to claim 29, comprising illuminating the photosynthetic cells.

31. A method according to claim 30, wherein illuminating the photosynthetic cells comprises illuminating the photosynthetic cells from within the body.

32. An implantable device for treating a medical disorder comprising a chamber which is configured to be implanted in a body of an individual, the chamber holding:
   isolated functional cells that remove a substance from the body for treatment of the medical disorder, the chamber having a wall that is permeable to the substance; and
   photosynthetic cells that convert carbon dioxide to oxygen when illuminated,
   wherein the device, when entirely implanted within the body, is configured such that the photosynthetic cells can be illuminated.

33. A method of treating a medical disorder comprising:
   providing the device of claim 32;
   implanting the device in a body of an individual such that the photosynthetic cells can be illuminated; and
   when said device is implanted in the body, removing a substance from the body with said device.

* * * * *